United States Patent
Lentz et al.

(10) Patent No.: US 7,156,840 B2
(45) Date of Patent: Jan. 2, 2007

(54) PRESSURE MONITOR FOR CRYOABLATION CATHETER

(75) Inventors: David J. Lentz, La Jolla, CA (US); Eric Ryba, San Diego, CA (US)

(73) Assignee: Cryocor, Inc., San Diego, CA (US)

( * ) Notice: Subject to any disclaimer, the term of this patent is extended or adjusted under 35 U.S.C. 154(b) by 204 days.

(21) Appl. No.: 10/880,233

(22) Filed: Jun. 29, 2004

(65) Prior Publication Data
US 2005/0288657 A1 Dec. 29, 2005

(51) Int. Cl.
*A61B 18/18* (2006.01)

(52) U.S. Cl. .......................... 606/21; 606/20; 606/22; 606/23

(58) Field of Classification Search ............. 606/20–23
See application file for complete search history.

(56) References Cited

U.S. PATENT DOCUMENTS

| | | | |
|---|---|---|---|
| 3,696,813 A | 10/1972 | Wallach | |
| 3,913,581 A | 10/1975 | Ritson et al. | |
| 4,018,227 A | 4/1977 | Wallach | |
| 5,139,496 A | 8/1992 | Hed | |
| 5,281,213 A | 1/1994 | Milder et al. | |
| 5,281,215 A | 1/1994 | Milder | |
| 5,423,807 A * | 6/1995 | Milder ........................ | 606/20 |
| 5,759,182 A | 6/1998 | Varney et al. | |
| 5,876,399 A | 3/1999 | Chia et al. | |
| 5,899,898 A | 5/1999 | Arless et al. | |
| 5,899,899 A | 5/1999 | Arless et al. | |
| 5,992,158 A | 11/1999 | Goddard et al. | |
| 6,024,740 A | 2/2000 | Lesh et al. | |
| 6,048,919 A | 4/2000 | McCullough | |
| 6,117,101 A | 9/2000 | Diederich et al. | |
| 6,139,544 A | 10/2000 | Mikus et al. | |
| 6,235,019 B1 | 5/2001 | Lehmann et al. | |
| 6,251,105 B1 | 6/2001 | Mikus et al. | |
| 6,280,439 B1 | 8/2001 | Martin et al. | |
| 6,283,959 B1 | 9/2001 | Lalonde et al. | |
| 6,383,180 B1 | 5/2002 | Lalonde et al. | |
| 6,407,149 B1 | 6/2002 | McCullough | |
| 6,440,126 B1 * | 8/2002 | Abboud et al. ................ | 606/22 |
| 6,468,268 B1 * | 10/2002 | Abboud et al. ................ | 606/20 |
| 6,471,693 B1 | 10/2002 | Carroll et al. | |
| 6,471,694 B1 * | 10/2002 | Kudaravalli et al. .......... | 606/21 |
| 6,527,769 B1 | 3/2003 | Langberg et al. | |
| 6,540,740 B1 | 4/2003 | Lehmann et al. | |
| 6,562,030 B1 | 5/2003 | Abboud et al. | |

(Continued)

*Primary Examiner*—Roy D. Gibson
*Assistant Examiner*—Alex Toy
(74) *Attorney, Agent, or Firm*—Nydegger & Associates

(57) ABSTRACT

A cryoablation device having a pressure monitoring system includes an elongated catheter tube that has a central lumen and is formed with a closed distal end. The distal end of a refrigerant supply line is positioned in the central lumen and distanced from the catheter tube's distal end to establish an expansion chamber therebetween. A return line, which can be established between the supply line and the catheter tube or can include a return tube, is provided to exhaust expanded refrigerant from the chamber. First and second pressure sensors are respectively positioned in the supply line upstream from the expansion chamber and in the return line. Typically, both sensors are positioned to remain at extracorporeal locations throughout a cryoablation procedure. Measured pressures are used together with the supply and return line dimensions to analytically estimate the chamber pressure and allow the expansion of refrigerant in the chamber to be monitored.

19 Claims, 1 Drawing Sheet

U.S. PATENT DOCUMENTS

| | | |
|---|---|---|
| 6,569,158 B1 | 5/2003 | Abboud et al. |
| 6,575,966 B1 | 6/2003 | Lane et al. |
| 6,579,287 B1 | 6/2003 | Wittenberger et al. |
| 6,585,728 B1 | 7/2003 | Heiner et al. |
| 6,585,729 B1 | 7/2003 | Eum |
| 6,589,234 B1 | 7/2003 | Lalonde et al. |
| 6,592,577 B1 | 7/2003 | Abboud et al. |
| 6,605,087 B1 | 8/2003 | Swartz et al. |
| 6,635,053 B1 | 10/2003 | Lalonde et al. |
| 6,733,494 B1 | 5/2004 | Abboud et al. |
| 6,755,823 B1 | 6/2004 | Lalonde |
| 6,761,714 B1 | 7/2004 | Abboud et al. |
| 2001/0021847 A1 | 9/2001 | Abboud et al. |
| 2001/0025075 A1 | 9/2001 | Smith et al. |
| 2002/0025998 A1 | 2/2002 | McCullough et al. |
| 2002/0045894 A1* | 4/2002 | Joye et al. .................. 606/21 |
| 2002/0062122 A1 | 5/2002 | Lehmann et al. |
| 2002/0111612 A1 | 8/2002 | Lalonde et al. |
| 2002/0115989 A1 | 8/2002 | Abboud et al. |
| 2003/0004504 A1 | 1/2003 | Abboud et al. |
| 2003/0009160 A1 | 1/2003 | Carroll et al. |
| 2003/0018326 A1 | 1/2003 | Abboud et al. |
| 2003/0097124 A1 | 5/2003 | Lehmann et al. |
| 2004/0049178 A1 | 3/2004 | Abboud et al. |
| 2004/0054361 A1 | 3/2004 | Lehmann et al. |
| 2005/0215989 A1* | 9/2005 | Abboud et al. ............ 606/21 |

* cited by examiner

PRESSURE MONITOR FOR CRYOABLATION CATHETER

FIELD OF THE INVENTION

The present invention pertains generally to devices and methods for cryoablating internal tissue. More particularly, the present invention pertains to devices and methods for monitoring the pressure inside the expansion chamber of a cryoablation catheter. The present invention is particularly, but not exclusively, useful for monitoring pressures at the tip of a cryoablation catheter using pressure sensors that remain extracorporeally positioned during a cryoablation procedure.

BACKGROUND OF THE INVENTION

The non-invasive cryoablation of tissue within the vasculature (e.g. the veins, arteries and chambers of the heart) of a patient can be used to effectively destroy or isolate diseased tissue. For example, atrial fibrillation, which is a somewhat common heart condition, can be treated by cryoablating a circumferential band of tissue surrounding the ostium where a pulmonary vein connects with the left atrium to prevent abnormal electrical signals from reaching the heart. To perform such a procedure, the tip of a cryoablation catheter is typically inserted into and advanced within the vasculature of a patient until the tip is located adjacent to the targeted tissue. Next, in a typical cryocatheter, a refrigerant is pumped into the catheter for expansion into an expansion chamber that is located at or near the catheter tip. The expansion of the refrigerant cools the catheter tip and target tissue.

One way to monitor and control the expansion of a refrigerant near the distal tip of a cryocatheter is to monitor the pressure within the expansion chamber. In particular, the measured pressure within the chamber provides an indication of the flow of refrigerant through the tip, which in turn, provides an indication of the instantaneous cooling power of the cryocatheter. In addition, for a cryoablation system in which the refrigerant undergoes a phase change during expansion (i.e. transitions from a liquid to a gaseous state), the measured chamber pressure provides an indication of the actual refrigerant boiling temperature. This boiling temperature provides a direct indication of the temperature of the cryoablation catheter tip. Moreover, the measured chamber pressure can be used continuously during an ablation procedure to vary the flow of refrigerant into the catheter to optimize both the tip temperature and the catheter's cooling power.

With the above in mind, there are several drawbacks associated with placing a pressure sensor directly in the expansion chamber of a cryocatheter. First, such a positioning scheme uses up critical space at the distal tip of the catheter. More specifically, placing the pressure sensor at the tip results in either a reduction in expansion chamber volume or an increase in catheter tip size. The former can cause a reduction in refrigerant flow which can effectively lower the cooling power of the cryocatheter. On the other hand, increasing the tip size reduces the likelihood that the catheter tip can successfully navigate through the vasculature and reach the treatment site. As is well known, the human vasculature is curved, branched and contains vessels having relatively small inner diameters. As a consequence, it is necessary to design a catheter having a relatively low profile to allow the distal end of the catheter to navigate through the complex vasculature.

In addition to space considerations, the expansion chamber presents a relatively harsh environment for a pressure sensor. Specifically, a sensor positioned in the expansion chamber must be operable over a wide range of temperatures, including cryogenic temperatures as low as minus 85 degrees C., or lower.

In light of the above, it is an object of the present invention to provide systems and methods for measuring the pressure within an expansion chamber at the distal end of a cryocatheter which do not require a reduction in the size of the chamber or an increase in the size of the catheter tip. It is still another object of the present invention to provide a system for measuring an expansion chamber pressure with pressure sensors that remain positioned at extracorporeal locations during a cryocatheter procedure. Yet another object of the present invention is to provide systems and methods for monitoring the temperature and cooling power of a cryocatheter tip which are easy to use, relatively simple to implement, and comparatively cost effective.

SUMMARY OF THE INVENTION

The present invention is directed to a cryoablation device having a pressure monitoring system. For the present invention, the device includes an elongated catheter tube that has a central lumen and is formed with a closed distal end. The device further includes a refrigerant supply unit which is connected to the proximal end of a supply line. The other end of the supply line (i.e. the distal end) is positioned in the central lumen of the catheter tube and distanced from the catheter tube's distal end. With this cooperation of structure, an expansion chamber is established in the central lumen between the distal end of the supply tube and the closed distal end of the catheter tube.

In a typical embodiment, the supply line includes a supply tube and a capillary tube with the capillary tube attached to the distal end of the supply tube. With this combination, the refrigerant supply unit can be activated to introduce a regulated flow of refrigerant into the supply tube for subsequent flow through the capillary tube. From the capillary tube, the refrigerant expands into the expansion chamber absorbing heat as it expands.

For the present invention, the device also includes a return line to exhaust expanded refrigerant from the expansion chamber. In a first embodiment, the return line includes a return tube having a distal end that is disposed in the central lumen of the catheter tube. Typically, the distal end of the return tube is positioned to be coterminous with the distal end of the supply line (e.g. the distal end of the capillary tube). The other end of the return tube (i.e. the proximal end) typically remains at an extracorporeal location throughout a cryoablation procedure.

The monitoring system of the cryoablation device includes a first pressure sensor that is positioned in the supply line at a pre-selected distance upstream from the expansion chamber. Typically, the pre-selected distance is chosen to ensure that the first pressure sensor remains at an extracorporeal location throughout a cryoablation procedure. Functionally, the first pressure sensor measures a supply pressure, $P_s$, in the supply line. In addition, the device includes a second pressure sensor that is positioned in the return tube at a pre-selected distance downstream from the expansion chamber. Typically, the pre-selected distance is chosen to ensure that the second pressure sensor remains at an extracorporeal location throughout a cryoablation procedure. Functionally, the second pressure sensor measures a return pressure, $P_r$, in the return line.

Using the measured pressures $P_s$ and $P_r$, the pressure in the expansion chamber can be determined to monitor the expansion of the refrigerant in the chamber. For example, $P_s$ and $P_r$ can be used to analytically estimate the chamber pressure because the supply line and return line are contiguous and have known dimensions. Alternatively, an empirical relationship between $P_s$, $P_r$, and the chamber pressure can be developed and used to estimate the chamber pressure once the pressures $P_s$ and $P_r$ have been measured.

In another embodiment of the cryoablation device, a return tube is not used. Instead, a return line is established between the supply line and catheter tube. For example, the return line can be established between the inner surface of the catheter tube and the outer surface of the supply line (e.g. the outer surfaces of the supply tube and capillary tube). For this embodiment, the second pressure sensor is typically positioned between the supply tube and catheter tube and at a pre-selected distance downstream from the expansion chamber to measure a return pressure, $P_r$, in the return line.

Some embodiments of the cryoablation device include a control unit having an electronic processor that is connected to the first and second pressure sensors. The processor can be programmed to calculate the expansion chamber pressure using either an analytical approach, an empirical approach or a combination thereof. Once the expansion chamber pressure has been calculated, the processor can compare the pressure in the expansion chamber with a reference pressure to create an error signal. In addition, the processor can be configured to control the regulated flow of refrigerant into the supply tube. Specifically, the processor can vary the flow of refrigerant into the supply tube until the error signal is a nullity and a pre-selected chamber pressure has been obtained.

In some implementations of the device, the monitoring system can be configured to detect refrigerant leaks by comparing the flow of refrigerant into the supply line with the flow of refrigerant exiting the device through the return line. If a leak is detected, the processor can limit or stop the flow of refrigerant into the supply line.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
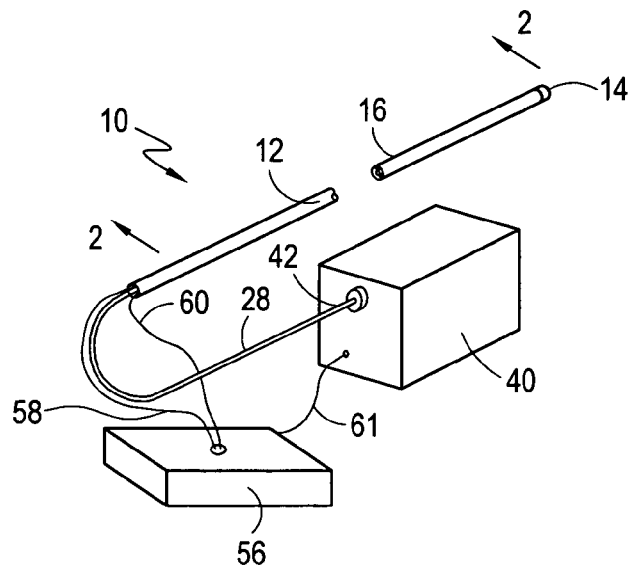
FIG. 1 is a simplified, perspective view of a device for cryoablating tissue at an internal treatment site.

Referring to FIG. 1, a device for cryoablating tissue at an internal treatment site is shown and generally designated 10. As shown in FIG. 1, the device 10 includes a catheter 12, the distal end of which is typically inserted into the vasculature of a patient (not shown) and advanced to a treatment site. With the distal end of the catheter 12 positioned at a treatment site, an operative surface such as surface 14 can be cooled to a cryogenic temperature (e.g. minus −85 degrees Celsius) and placed in contact with selected internal tissue to cryoablate both contacted and surrounding tissue. Cryoablation of tissue can be performed for a variety of purposes including, but not limited to, the destruction or isolation of diseased tissue. In one application, cryoablation can be used to form conduction blocks to prevent unwanted electrical signals from originating or passing through a specific portion of a patient's body. For example, in one procedure that is useful in treating patients suffering from atrial fibrillation, conduction blocks are formed to prevent abnormal electrical signals originating in or passing through a pulmonary vein from reaching the heart.

Figure 2:
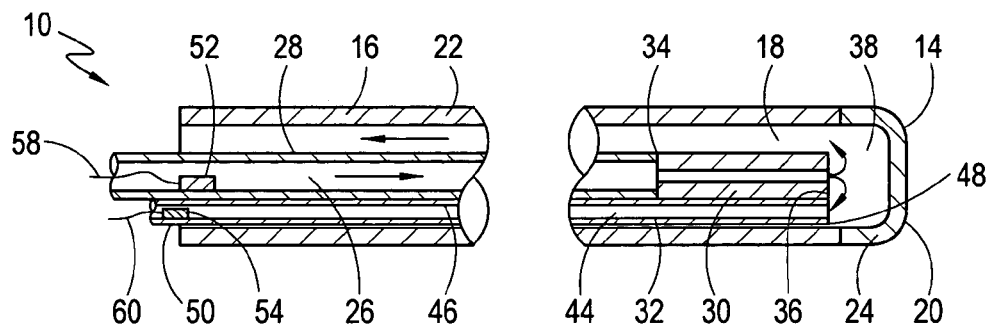
FIG. 2 is a cross-sectional view of a portion of the device shown in FIG. 1 as seen along 2—2 in FIG. 1.

With cross-reference now to FIGS. 1 and 2, it can be seen that the device 10 includes an elongated catheter tube 16 that has a central lumen 18 and is formed with a closed distal end 20. As best seen in FIG. 2, the catheter tube 16 includes a relatively flexible, thermally insulating proximal portion 22 which, for example can be made of a PEBAX material and a distal portion 24 which is typically made of a conductive metal. Also, the device 10 includes a supply line 26, the distal portion of which is positioned in the central lumen 18 of the catheter tube 16. For the embodiment shown, the supply line 26 includes a supply tube 28 and a capillary tube 30.

As further shown in FIG. 2, the proximal end 32 of the capillary tube 30 is attached to the distal end 34 of the supply tube 28, and both the supply tube 28 and capillary tube 30 are arranged to be substantially co-axial with the catheter tube 16. FIG. 2 further shows that the distal end 36 of the capillary tube 30 is distanced from the distal end 20 of the catheter tube 16 to thereby establish an expansion chamber 38 between the distal end 36 of the capillary tube 30 and the distal end 20 of the catheter tube 16.

As best seen in FIG. 1, the device 10 also includes a refrigerant supply unit 40 which is connected to the proximal end 42 of the supply tube 28. With this combination, the refrigerant supply unit 40 can be activated to introduce a regulated flow of refrigerant into the supply tube 28 for subsequent flow through the capillary tube 30 (FIG. 2). From the capillary tube 30, the refrigerant expands into the expansion chamber 38 absorbing heat as it expands and cooling the distal portion 24 of the catheter tube 16 and the operative surface 14.

In one embodiment of the device 10, a fluid refrigerant is used that transitions from a liquid state to a gaseous state as it expands into the expansion chamber 38. A suitable refrigerant supply unit 40 for delivering a refrigerant in a liquid state to the distal end 36 of a capillary tube 30 for transition to a gaseous state in the expansion chamber 38 is disclosed in co-pending U.S. patent application Ser. No. 10/243,997, entitled "A Refrigeration Source for a Cryoablation Catheter" and filed on Sep. 12, 2002, which is assigned to the same assignee as the present invention. Co-pending U.S. application Ser. No. 10/243,997 is incorporated by reference herein. Heat absorbed by the refrigerant during this phase transition (i.e. latent heat) cools the distal portion 24 of the catheter tube 16 and the operative surface 14. When the proper pressure is established in the expansion chamber 38, a refrigerant such as nitrous oxide can be expanded to cool the distal portion 24 of the catheter tube 16 and the operative surface 14 to a temperature of approximately −85 degrees Celsius.

The device 10 also includes a return line 44, which for the embodiment shown in FIG. 2, includes a return tube 46, to exhaust expanded refrigerant from the expansion chamber 38. In a typical embodiment, the distal end 48 of the return tube 46 is positioned to be coterminous with the distal end 36 of the capillary tube 30, as shown. The proximal end 50 of the return tube 46 typically remains at an extracorporeal location throughout a cryoablation procedure. If desired, the proximal end 50 of the return tube 46 can be connected to a reservoir (not shown) to allow for refrigerant capture or recycling.

Continuing with FIG. 2, it can be seen that the device 10 includes a pressure sensor 52 that is positioned in the supply tube 28 at a pre-selected distance upstream from the expansion chamber 38. Typically, the pre-selected distance is chosen to ensure that the pressure sensor 52 remains at an extracorporeal location throughout a cryoablation procedure. Functionally, the pressure sensor 52 measures a supply pressure, $P_s$, in the supply line 26. In addition, the device 10 includes a pressure sensor 54 that is positioned in the return tube 46 at a pre-selected distance downstream from the expansion chamber 38. Typically, the pre-selected distance is chosen to ensure that the pressure sensor 54 remains at an extracorporeal location throughout a cryoablation procedure. Functionally, the second pressure sensor 54 measures a return pressure, $P_r$, in the return line 44.

With cross-reference to FIGS. 1 and 2, it can be seen that the cryoablation device 10 includes a control unit 56 having an electronic processor that is connected to each of the pressure sensors 52, 54 via respective wires 58, 60. The processor can be programmed to calculate the expansion chamber pressure using either an analytical approach, an empirical approach or a combination thereof. Inputs to the processor for determining the expansion chamber pressure can include one or more of the following: the measured pressures $P_s$ and $P_r$, the dimensions of the supply line 26 and return line 44 to include the respective lengths and lumen diameters for both the supply line 26 and return line 44, and empirically derived data relating $P_s$, $P_r$, and the chamber pressure.

Once the expansion chamber pressure has been calculated, the processor can compare the pressure in the expansion chamber 38 with a reference pressure to create an error signal. For the device 10, the processor of the control unit 56 can be configured to control the regulated flow of refrigerant from the refrigerant supply unit 40 into the supply tube 28. Specifically, the processor is connected via wire 61 to a regulator or similar component in the refrigerant supply unit 40 to vary the flow of refrigerant into the supply tube 28 until the error signal is a nullity and a pre-selected chamber pressure has been obtained.

In some implementations of the device 10, the monitoring system can be configured to detect refrigerant leaks by comparing the flow of refrigerant into the supply line 26 with the flow of refrigerant out of the return line 44 using the measure pressures $P_s$ and $P_r$. If a leak is detected, the processor in the control unit 56 can limit or stop the flow of refrigerant into the supply line 26.

Figure 3:
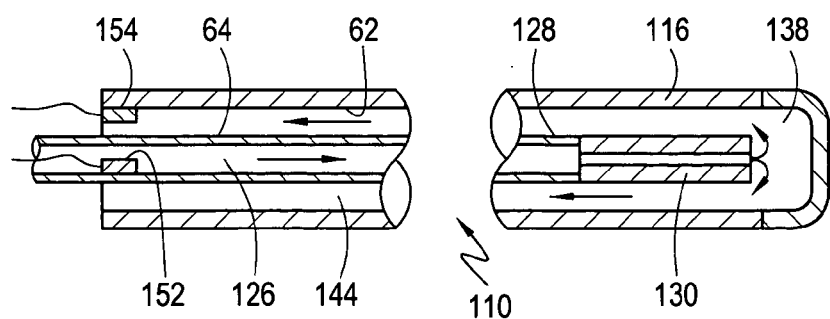
FIG. 3 is a cross-sectional view as in FIG. 2 of an alternate embodiment in which a return line is established in the space between the catheter tube and the supply line.

FIG. 3 shows another embodiment of a cryoablation device (designated device 110). As shown, in this embodiment, a return line 144 is established between the supply line 126 (which includes supply tube 128 and capillary tube 130) and catheter tube 116. In greater detail, the return line 144 is established between the inner surface 62 of the catheter tube 116 and the outer surface 64 of the supply line 126. For this embodiment, as shown, the pressure sensor 152 is positioned in the supply tube 128 to measure a supply pressure, $P_s$, in the supply line 126. Also, the pressure sensor 154 is positioned in the return line 144 between the supply tube 128 and catheter tube 116 to measure a return pressure, $P_r$, in the return line 144. FIG. 3 further shows that both sensors 152, 154 are positioned at respective pre-selected distances from the expansion chamber 138.

While the particular pressure monitor for cryoablation catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A cryoablation device having a pressure monitoring system, said device comprising:
    a refrigerant supply unit;
    an elongated catheter tube having a central lumen and formed with a closed distal end;
    a supply line having a proximal end connected to said refrigerant supply unit and a distal end disposed in said central lumen of said catheter tube and distanced from the distal end thereof to establish an expansion chamber therebetween, said supply line for delivering a refrigerant from said refrigerant supply unit to said expansion chamber for expansion therein;
    a return line in fluid communication with said expansion chamber for exhausting refrigerant from said expansion chamber;
    a first pressure sensor for measuring a supply pressure, $P_s$, in said supply line at a pre-selected distance upstream from said expansion chamber;
    a second pressure sensor for measuring a return pressure, $P_r$, in said return line at a pre-selected distance downstream from said expansion chamber; and
    a control unit connected to said first pressure sensor and to said second pressure sensor for using said measured pressures $P_s$ and $P_r$ for determining a pressure in said expansion chamber to monitor the expansion of said refrigerant therein.

2. A device as recited in claim 1 wherein said return line comprises a return tube having a distal end disposed in said central lumen of said catheter tube.

3. A device as recited in claim 2 wherein said distal end of said return tube is positioned to be substantially coterminous with said distal end of said supply line.

4. A device as recited in claim 1 wherein said catheter tube has an inner surface, said supply line has an outer surface and said return line is established between said inner surface of said catheter tube and said outer surface of said supply line.

5. A device as recited in claim 1 wherein said supply line comprises a supply tube and a capillary tube, said supply tube is formed with a lumen having a lumen diameter, D, and said capillary tube is formed with a lumen having a lumen diameter, d, with D >d.

6. A device as recited in claim 5 wherein said supply tube and said catheter tube are arranged co-axially.

7. A device as recited in claim 1 wherein said control unit further comprises:
    a means for comparing the pressure in said expansion chamber with a reference pressure to create an error signal; and
    a means for varying said supply pressure, $P_s$, to make the error signal a nullity.

8. A device as recited in claim 7 further comprising an alarm means responsive to the error signal for shutting down the flow of refrigerant from said refrigerant supply unit and into said supply line when the error signal attains a predetermined value.

9. A system for monitoring pressure in an expansion chamber of a cryoablation catheter, said catheter having a supply line for delivering a refrigerant to said expansion chamber for expansion therein and a return line for exhausting expanded refrigerant therefrom, said system comprising:
- a first pressure sensor for measuring a supply pressure, $P_s$, in said supply line at a pre-selected distance upstream from said expansion chamber;
- a second pressure sensor for measuring a return pressure, $P_r$, in said return line at a pre-selected distance downstream from said expansion chamber; and
- a control unit for using said measured pressures $P_s$ and $P_r$ to determine the pressure in said expansion chamber to monitor the expansion of said refrigerant therein.

10. A system as recited in claim 9 wherein said control unit is configured to use at least one supply line dimension and at least one return line dimension together with said measured pressures $P_s$ and $P_r$ to determine the pressure in said expansion chamber.

11. A system as recited in claim 10 wherein said system further comprises:
- an electronic means for comparing the pressure in said expansion chamber with a reference pressure to create an error signal; and
- a means for varying said supply pressure, $P_s$, to make the error signal a nullity.

12. A system as recited in claim 11 further comprising an alarm means responsive to the error signal for shutting down the flow of refrigerant from said refrigerant supply unit and into said supply line when the error signal attains a predetermined value.

13. A method for cryoablating tissue at a treatment site in the vasculature of a patient, said method comprising the steps of:
- providing an elongated catheter tube having a central lumen and formed with a closed distal end;
- positioning the distal end of a supply line in said central lumen of said catheter tube at a distance from said distal end thereof to establish an expansion chamber therebetween;
- advancing said distal end of said catheter tube through the patient's vasculature to the treatment site;
- introducing a refrigerant into said supply line for outflow from said distal end thereof and expansion in said expansion chamber;
- measuring a supply pressure, $P_s$, at an extracorporeal location in said supply line upstream from said expansion chamber;
- measuring a return pressure, $P_r$, at an extracorporeal location downstream from said expansion chamber; and
- using said measured pressures $P_s$ and $P_r$ to determine a pressure in said expansion chamber to monitor the expansion of said refrigerant therein.

14. A method as recited in claim 13 further comprising the step of positioning a return tube in said central lumen of said catheter, and wherein said step of measuring a return pressure, $P_r$, is accomplished by measuring a pressure within said return tube.

15. A method as recited in claim 14 wherein said distal end of said return tube is positioned to be substantially coterminous with said distal end of said supply line.

16. A method as recited in claim 13 wherein said catheter tube has an inner surface, said supply line has an outer surface and wherein said step of measuring a return pressure, $P_r$, is accomplished by measuring a pressure between said inner surface of said catheter tube and said outer surface of said supply line.

17. A method as recited in claim 13 wherein said supply line comprises a supply tube and a capillary tube, said supply tube is formed with a lumen having a lumen diameter, $D$, and said capillary tube is formed with a lumen having a lumen diameter, $d$, with $D > d$.

18. A method as recited in claim 17 wherein said supply tube and said catheter tube are arranged co-axially.

19. A method as recited in claim 13 further comprising the step of varying the flow of refrigerant into said supply line to obtain a pre-selected pressure in said expansion chamber.

* * * * *